United States Patent
Lee et al.

(10) Patent No.: US 7,585,979 B2
(45) Date of Patent: Sep. 8, 2009

(54) PROCESS FOR PREPARING N-HYDROXY-4-{5-[4-(5-ISOPROPYL-2-METHYL-1,3-THIAZOL-4-YL)-PHENOXY]-PENTOXY}-BENZAMIDINE

(75) Inventors: Jin Soo Lee, Yongin-si (KR); Seok Hoon Ahn, Seoul (KR); Young Goo Jin, Seoul (KR); Jae Hoon Park, Seoul (KR); Dong Hyuk Shin, Gunpo-si (KR); Eun Hee Cho, Suwon-si (KR); Hwan Bong Chang, Suwon-si (KR); Young Ho Jung, Seongnam-si (KR)

(73) Assignee: Dong Wha Pharmaceutical Ind. Co., Ltd., Seoul (KR)

( * ) Notice: Subject to any disclaimer, the term of this patent is extended or adjusted under 35 U.S.C. 154(b) by 95 days.

(21) Appl. No.: 11/631,829

(22) PCT Filed: Jul. 5, 2005

(86) PCT No.: PCT/KR2005/002137

§ 371 (c)(1),
(2), (4) Date: Jan. 22, 2008

(87) PCT Pub. No.: WO2006/004368

PCT Pub. Date: Jan. 12, 2006

(65) Prior Publication Data

US 2008/0125596 A1   May 29, 2008

(30) Foreign Application Priority Data

Jul. 5, 2004   (KR) ............ 10-2004-0052070

(51) Int. Cl.
*C07D 277/20* (2006.01)
(52) U.S. Cl. ........................ 548/202
(58) Field of Classification Search ............ None
See application file for complete search history.

(56) References Cited

U.S. PATENT DOCUMENTS 5,451,700 A * 9/1995 Morrissey et al. ......... 564/165
6,150,390 A * 11/2000 Suh et al. .................. 514/379
2004/0186150 A1 * 9/2004 Suh et al. .................. 514/365

OTHER PUBLICATIONS

Sung-eun Lee, Doctoral Dissertation, Department of Chemistry, Graduate School oF Arts and Science, Busan University, South Korea, Aug. 1999.*

\* cited by examiner

*Primary Examiner*—Kamal A Saeed
(74) *Attorney, Agent, or Firm*—Casimir Jones, S.C.

(57) ABSTRACT

This invention relates to an improved method of preparing N-hydroxy-4-{5-[4-(5-isopropyl-2-methyl-1,3-thiazol-4-yl)phenoxy]pentoxy}benzamidine.

7 Claims, No Drawings

PROCESS FOR PREPARING N-HYDROXY-4-{5-[4-(5-ISOPROPYL-2-METHYL-1,3-THIAZOL-4-YL)-PHENOXY]-PENTOXY}-BENZAMIDINE

TECHNICAL FIELD

The present invention relates to an improved method of preparing N-hydroxy-4-{5-[4-(5-isopropyl-2-methyl-1,3-thiazol-4-yl)phenoxy]pentoxy}benzamidine.

BACKGROUND ART

A method of preparing N-hydroxy-4-{5-[4-(5-isopropyl-2-methyl-1,3-thiazol-4-yl)phenoxy]pentoxy}benzamidine, a known leukotriene $B_4$ receptor antagonist, is known (Lee, Sung-eun, Synthesis and Biological Activity of Natural Products and Designed New Hybrid Compounds for the Treatment of $LTB_4$ Related Disease, Ph.D thesis, Graduate School of Busan Univ., August 1999).

The preparation method of N-hydroxy-4-{5-[4-(5-isopropyl-2-methyl-1,3-thiazol-4-yl)phenoxy] pentoxy}benzamidine disclosed in the above literature includes preparing a compound (6) (Reaction 1 below), preparing a compound (9) (Reaction 2 below) and then reacting the compound (6) with the compound (9), to give an object compound (Reaction 3 below).

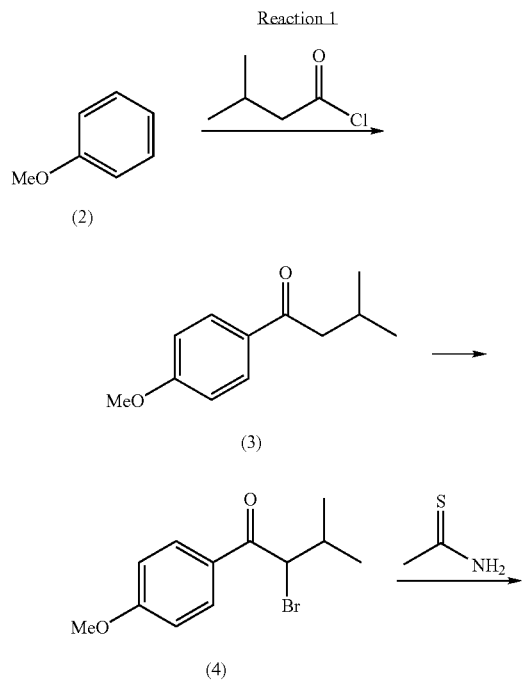

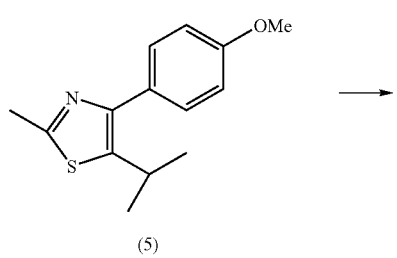

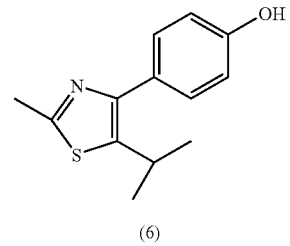

In Reaction 1, anisole (2) is reacted with isovaleryl chloride to afford a compound (3), which is then reacted with tetra-n-butylammoniumtribromide, thus preparing 2-bromo-1-(4-methoxy-phenyl)-3-methyl-butan-1-one (4) (yield: 77%). The above compound (4) is reacted with thioacetamide, to prepare a compound (5). The compound (5) is reacted with aluminum chloride using an ethanethiol and methylene chloride (1:1) solvent, therefore giving an intermediate compound (6) (yield: 79%).

However, tetra-n-butylammoniumtribromide (4) used in the above reaction is disadvantageous because it drastically decreases the preparation yield, and is expensive and difficult to handle and thus unsuitable for use in mass production. In addition, ethanethiol, which is a solvent used in the preparation of the intermediate compound (6), causes offensive odors, and has shortcomings making it unsuitable for use in mass production methods.

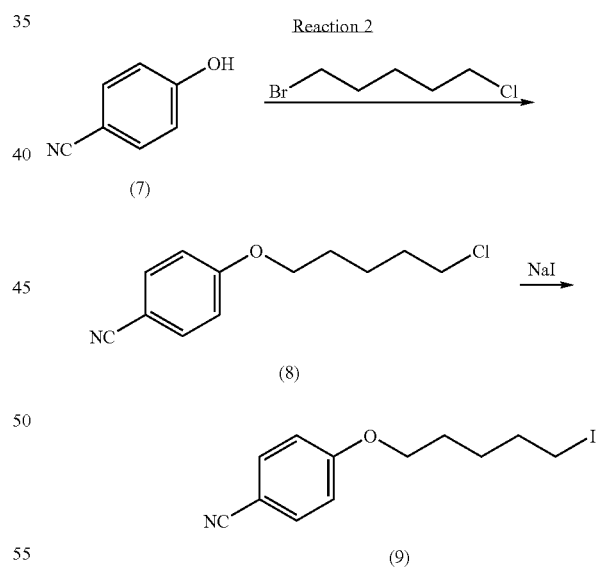

In Reaction 2, 4-hydroxy-benzonitrile (7) is reacted with 1-bromo-5-chloropentane to afford a compound (8), after which the compound (8) is reacted with sodium iodide, thus obtaining an intermediate compound (9) having an iodine group substituted for a chlorine group (yield: 89%).

However, the above process is disadvantageous because the preparation of the intermediate compound (9) requires two processes. Therefore, there is the need to improve the economy of the above process for mass production.

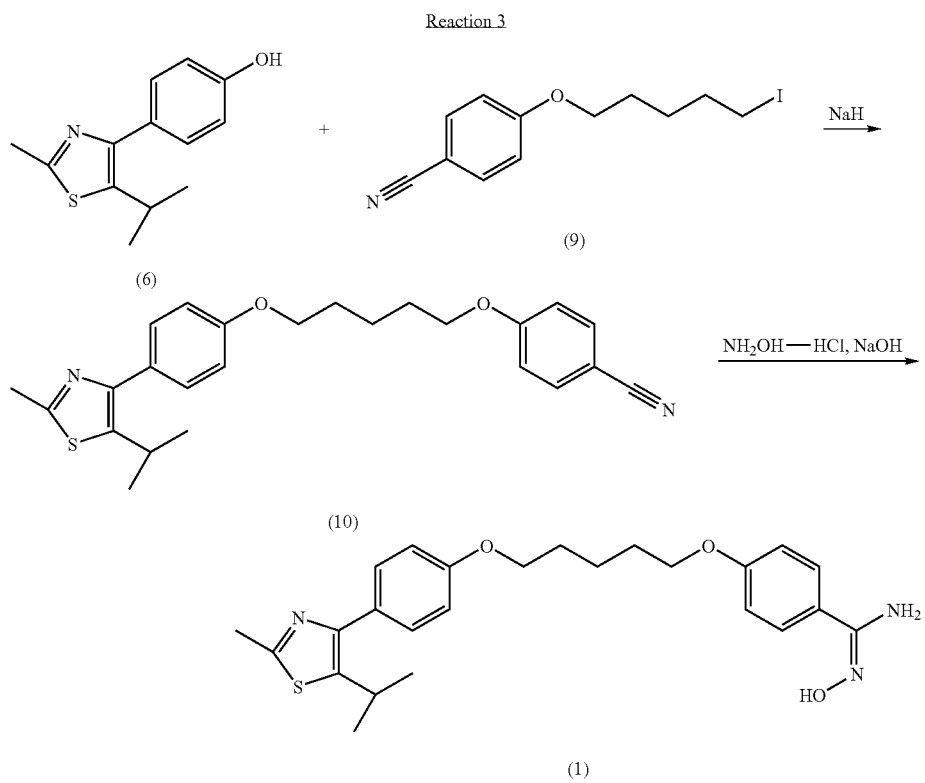

In Reaction 3, the compound (6) prepared through Reaction 1 and the compound (9) prepared through Reaction 2 are reacted with sodium hydride, giving a compound (10) (yield: 94%). Subsequently, the compound (10) is reacted with hydroxylamine hydrochloride and sodium hydroxide, thus preparing a final compound (1) (yield: 83%).

As such, sodium hydride, which serves as an acid reactor in the above reaction, is difficult to handle and unsuitable for use in mass production. Further, purification is conducted using column chromatography, which is difficult to apply to mass production, and also, the yield is decreased (total yield: about 24%).

Therefore, the present inventors have studied economical preparation methods, which have simple reaction processes and a drastically increased preparation yield, and are suitable for mass production, thus completing the present invention.

DISCLOSURE OF THE INVENTION

The present invention provides an improved method of preparing N-hydroxy-4-{5-[4-(5-isopropyl-2-methyl-1,3-thiazol-4-yl)phenoxy]pentoxy}benzamidine.

BEST MODE FOR CARRYING OUT THE INVENTION

The present invention provides an improved method of preparing N-hydroxy-4-{5-[4-(5-isopropyl-2-methyl-1,3-thiazol-4-yl)phenoxy]pentoxy}benzamidine, represented by Formula 1 below.

Formula 1

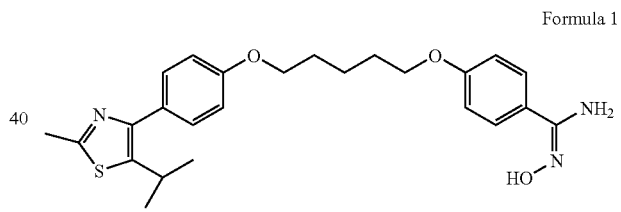

In the present invention, the improved method of preparing N-hydroxy-4-{5-[4-(5-isopropyl-2-methyl-1,3-thiazol-4-yl)phenoxy]pentoxy}benzamidine (1) comprises coupling 4-(5-isopropyl-2-methyl-1,3-thiazol-4-yl)-phenol (6), produced using anisole as a starting material, with 4-(5-chloro-pentoxy)-benzonitrile (8) or 4-(5-iodo-pentoxy)-benzonitrile (9), and reacting the obtained compound with hydroxylamine hydrochloride, thus preparing N-hydroxy-4-{5-[4-(5-isopropyl-2-methyl-1,3-thiazol-4-yl)phenoxy]pentoxy}benzamidine (1).

In the above preparation method of the present invention, the preparation of 4-(5-isopropyl-2-methyl-1,3-thiazol-4-yl)-phenol (6) includes steps of:

1) reacting anisole (2) with isovaleryl chloride, to prepare 1-(4-methoxy-phenyl)-3-methyl-butan-1-one (3), 2) reacting the compound (3) prepared in step 1) with bromine, sulfuryl chloride, N-bromosuccinimide or copper bromide, to prepare 2-halo-1-(4-methoxy-phenyl)-3-methyl-butan-1-one (4), 3) reacting the compound (4) prepared in step 2) with thioacetamide, to prepare 5-isopropyl-4-(4-methoxy-phenyl)-2-methyl-thiazole (5), and 4) reacting the compound (5) prepared in step 3) with bromic acid and acetic acid, sodium cyanide and dimethylsulfoxide, or tetrabutylammonium iodide and boron trifluoride·diethylether, to prepare 4-(5-isopropyl-2-methyl-1,3-thiazol-4-yl)-phenol (6).

In the above preparation method of the present invention, 4-(5-chloro-pentoxy)-benzonitrile (8) is prepared by reacting 4-hydroxy-benzonitrile with 1-bromo-5-chloropentane.

In the above preparation method of the present invention, the preparation of 4-(5-iodo-pentoxy)-benzonitrile (9) includes steps of:

1) reacting 4-hydroxy-benzonitrile (7) with 1-bromo-5-chloropentane, to prepare 4-(5-chloro-pentoxy)-benzonitrile (8), and 2) reacting the compound (8) prepared in step 1) with iodide, to prepare 4-(5-iodo-pentoxy)-benzonitrile (9).

Specifically, according to an aspect of the present invention, the preparation method comprises the following steps of:

1) reacting anisole (2) with isovaleryl chloride to prepare 1-(4-methoxy-phenyl)-3-methyl-butan-1-one (3), 2) reacting the compound (3) prepared in step 1) with bromine, sulfuryl chloride, N-bromosuccinimide or copper bromide, to prepare 2-halo-1-(4-methoxy-phenyl)-3-methyl-butan-1-one (4), 3) reacting the compound (4) prepared in step 2) with thioacetamide, to prepare 5-isopropyl-4-(4-methoxy-phenyl)-2-methyl-thiazole (5), 4) reacting the compound (5) prepared in step 3) with bromic acid and acetic acid, sodium cyanide and dimethylsulfoxide, or tetrabutylammonium iodide and boron trifluoride·diethylether, to prepare 4-(5-isopropyl-2-methyl-1,3-thiazol-4-yl)-phenol (6), 5) reacting 4-hydroxy-benzonitrile (7) with 1-bromo-5-chloropentane, to prepare 4-(5-chloro-pentoxy)-benzonitrile (8), 6) reacting the compound (6) obtained in step 4) with the compound (8) obtained in step 5) in the presence of sodium hydroxide, to prepare 4-{5-[4-(5-isopropyl-2-methyl-1,3-thiazol-4-yl)-phenoxy]-pentoxy}-benzonitrile (10), and 7) reacting the compound (10) prepared in step 6) with hydroxylamine hydrochloride and a base, to prepare N-hydroxy-4-{5-[4-(5-isopropyl-2-methyl-1,3-thiazol-4-yl)phenoxy]pentoxy}benzamidine (1), all steps of which are shown in Reaction 4, below:

Reaction 4

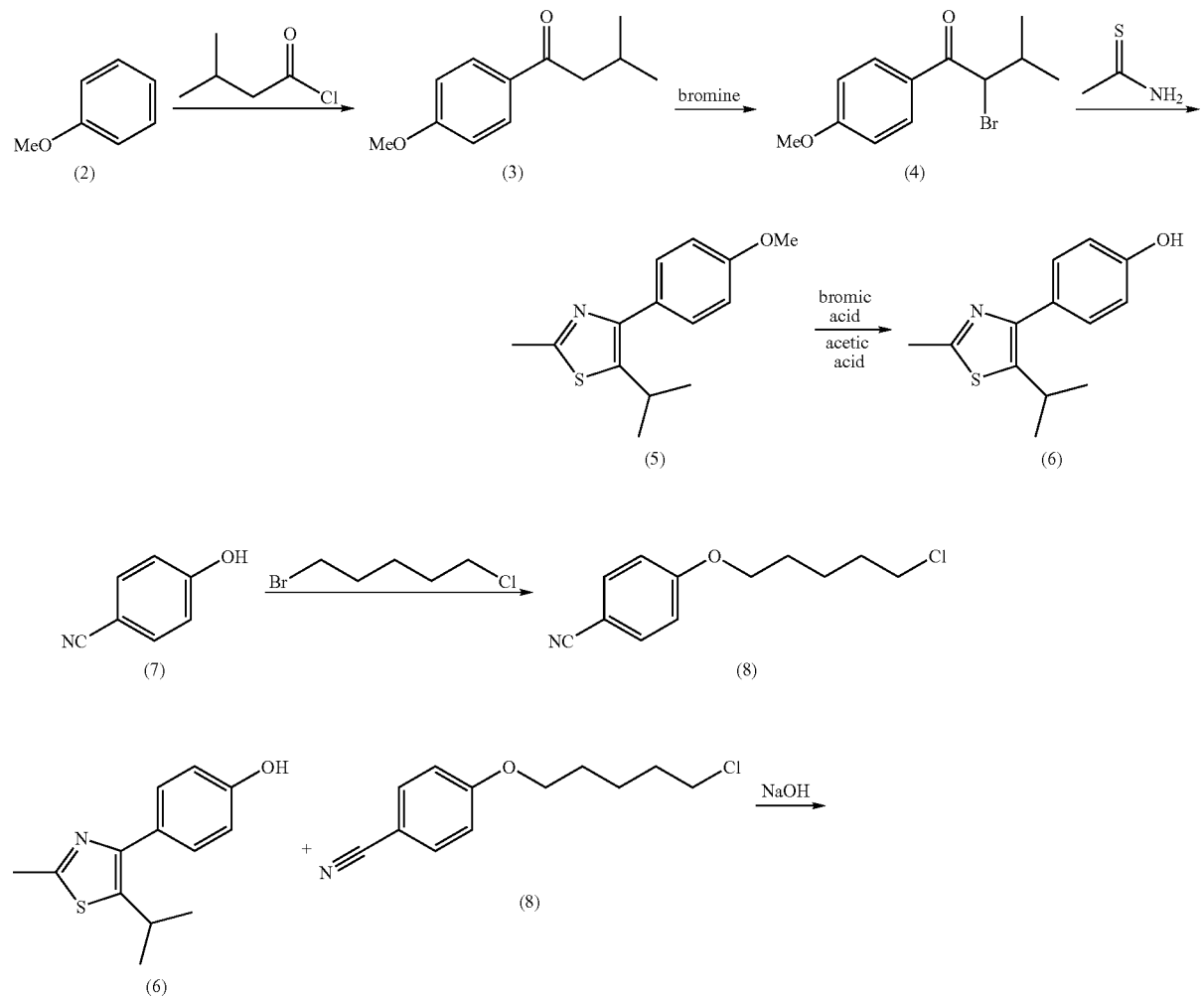

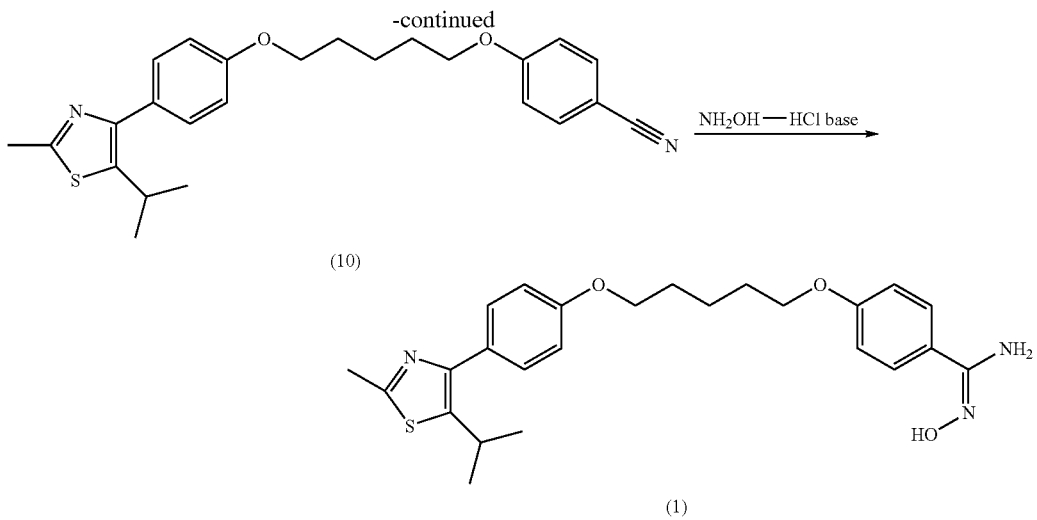

Below, each step of the improved method of preparing N-hydroxy-4-{5-[4-(5-isopropyl-2-methyl-1,3-thiazol-4-yl) phenoxy]pentoxy}benzamidine of the present invention is individually described.

In the first and second steps, after anisole (2) is reacted with isovaleryl chloride to afford 1-(4-methoxy-phenyl)-3-methyl-butan-1-one (3), the compound (3) is reacted with bromine, sulfuryl chloride, N-bromosuccinimide or copper bromide, to prepare 2-bromo-1-(4-methoxy-phenyl)-3-methyl-butan-1-one (4). At this time, the reaction temperature is preferably maintained in the range from −10 to 40° C., and the reaction solvent is selected from polar solvents, including dichloromethane, acetonitrile, ethylacetate, lower alcohols such as methanol, ethanol or isopropanol, ethers such as tetrahydrofuran or 1,4-dioxane, dimethylformamide, or dimethylsulfoxide, and mixtures thereof. Among the materials reacting with the compound (3) in the second step, bromine is preferably used because it is inexpensive and increases the yield (yield: 96% or more).

In the third step, the compound (4) prepared in the second step is reacted with thioacetamide, to afford 5-isopropyl-4-(4-methoxy-phenyl)-2-methyl-thiazole (5). As such, the reaction temperature is preferably maintained in the range from 20 to 100° C., and the reaction solvent is selected from polar solvents, including dichloromethane, acetonitrile, ethylacetate, lower alcohols such as methanol, ethanol or isopropanol, ethers such as tetrahydrofuran or 1,4-dioxane, dimethylformamide, or dimethylsulfoxide, and mixtures thereof.

In the fourth step, the compound (5) prepared in the third step is reacted with bromic acid and acetic acid, sodium cyanide and dimethylsulfoxide, or tetrabutylammonium iodide and boron trifluoride.diethylether, to afford 4-(5-isopropyl-2-methyl-1,3-thiazol-4-yl)-phenol (6). Conventionally, ethanethiol is used, whereby offensive odors occur and reagent handling is difficult to the extent of being unsuitable for use in mass production. However, in the present invention, the use of the compound (5) and the above materials reacting therewith, in particular, bromic acid and acetic acid result in decreased offensive odors, low price, simple reagent handling and a drastically increased preparation yield (yield: 84%).

In the fifth step, 4-hydroxy-benzonitrile (7) is reacted with 1-bromo-5-chloropentane, and thus, 4-(5-chloro-pentoxy)-benzonitrile (8) (yield: 90%) is obtained. As such, the reaction temperature is preferably maintained in the range from 20 to 82° C., and the reaction solvent is selected from polar solvents, including dichloromethane, acetonitrile, ethylacetate, lower alcohols such as methanol, ethanol or isopropanol, ethers such as tetrahydrofuran or 1,4-dioxane, dimethylformamide, or dimethylsulfoxide, and mixtures thereof. To ensure that the above reaction occurs under a basic condition, an inorganic base, including potassium carbonate, sodium hydroxide, potassium hydroxide, sodium amide, sodium hydride, sodium methoxide, or sodium ethoxide, and other base, may be used.

In the above reaction, the number of unnecessary steps is decreased compared to conventional methods, and the process is simplified, thus increasing the preparation yield (90%). In addition, the compound (8) may be crystallized under the appropriate reaction control without additional separation and purification, which is particularly useful in mass production methods.

In the sixth and seventh steps, the compound (6) prepared in the fourth step, and the compound (8) prepared in the fifth step are reacted in the presence of sodium hydroxide, thus preparing 4-{5-[4-(5-isopropyl-2-methyl-1,3-thiazol-4-yl)-phenoxy]-pentoxy}-benzonitrile (10) (yield: 90%). Further, the compound (10) is reacted with hydroxylamine hydrochloride and a base, therefore preparing N-hydroxy-4-{5-[4-(5-isopropyl-2-methyl-1,3-thiazol-4-yl)phenoxy] pentoxy}benzamidine (1) (yield: 95%). As such, the reaction solution is directly added with water, thereby being recrystallized, and hence, may be easily prepared on a large scale.

In the above reaction steps, the reaction temperature is preferably maintained in the range from room temperature to a solvent reflux temperature. The reaction solvent is selected from polar solvents, including dichloromethane, acetonitrile, ethylacetate, lower alcohols such as methanol, ethanol or isopropanol, ethers such as tetrahydrofuran or 1,4-dioxane, dimethylformamide, or dimethylsulfoxide, and mixtures thereof. The base used in the reaction is selected from organic base, including triethylamine, 1,8-diazabicyclo[5.4.0]undec-7-ene, DBU, diethylmethylamine (Et$_2$NMe), N-methylmorpholine, N-methylpiperidine, pyridine, 2,6-dimethylpyridine or from inorganic base, including potassium carbonate, potassium bicarbonate, sodium hydroxide, potassium hydroxide, sodium amide, sodium hydride, sodium methoxide, or sodium ethoxide, and other basic compounds. In the present invention, triethylamine is preferable, and is used in 1 to 4 equivalents.

Consequently, the total reaction yield (33%) of the preparation method shown in Reaction 4 was found to be remarkably higher than the total yield (24%) of the method disclosed in the above literature.

Specifically, according to another aspect of the present invention, the preparation method comprises the following steps of:

1) reacting anisole (2) with isovaleryl chloride, to prepare 1-(4-methoxy-phenyl)-3-methyl-butan-1-one (3), 2) reacting the compound (3) prepared in step 1) with bromine, sulfuryl chloride, N-bromosuccinimide or copper bromide, to prepare 2-halo-1-(4-methoxy-phenyl)-3-methyl-butan-1-one (4), 3) reacting the compound (4) prepared in step 2) with thioacetamide, to prepare 5-isopropyl-4-(4-methoxy-phenyl)-2-methyl-thiazole (5), 4) reacting the compound (5) prepared in step 3) with bromic acid and acetic acid, sodium cyanide and dimethylsulfoxide, or tetrabutylammonium iodide and boron trifluoride·diethylether, to prepare 4-(5-isopropyl-2-methyl-1,3-thiazol-4-yl)-phenol (6), 5) reacting 4-hydroxy-benzonitrile (7) with 1-bromo-5-chloropentane to afford 4-(5-chloro-pentoxy)-benzonitrile (8), which is then reacted with iodide, to prepare 4-(5-iodo-pentoxy)-benzonitrile (9), 6) reacting the compound (6) prepared in step 4) and the compound (9) prepared in step (5) in the presence of sodium hydroxide, to prepare 4-{5-[4-(5-isopropyl-2-methyl-1,3-thiazol-4-yl)-phenoxy]-pentoxy}-benzonitrile (10), and 7) reacting the compound (10) prepared in step 6) with hydroxylamine hydrochloride and a base, to prepare N-hydroxy-4-{5-[4-(5-isopropyl-2-methyl-1,3-thiazol-4-yl)phenoxy]pentoxy}benzamidine (1), all steps of which are shown in Reaction 5 below:

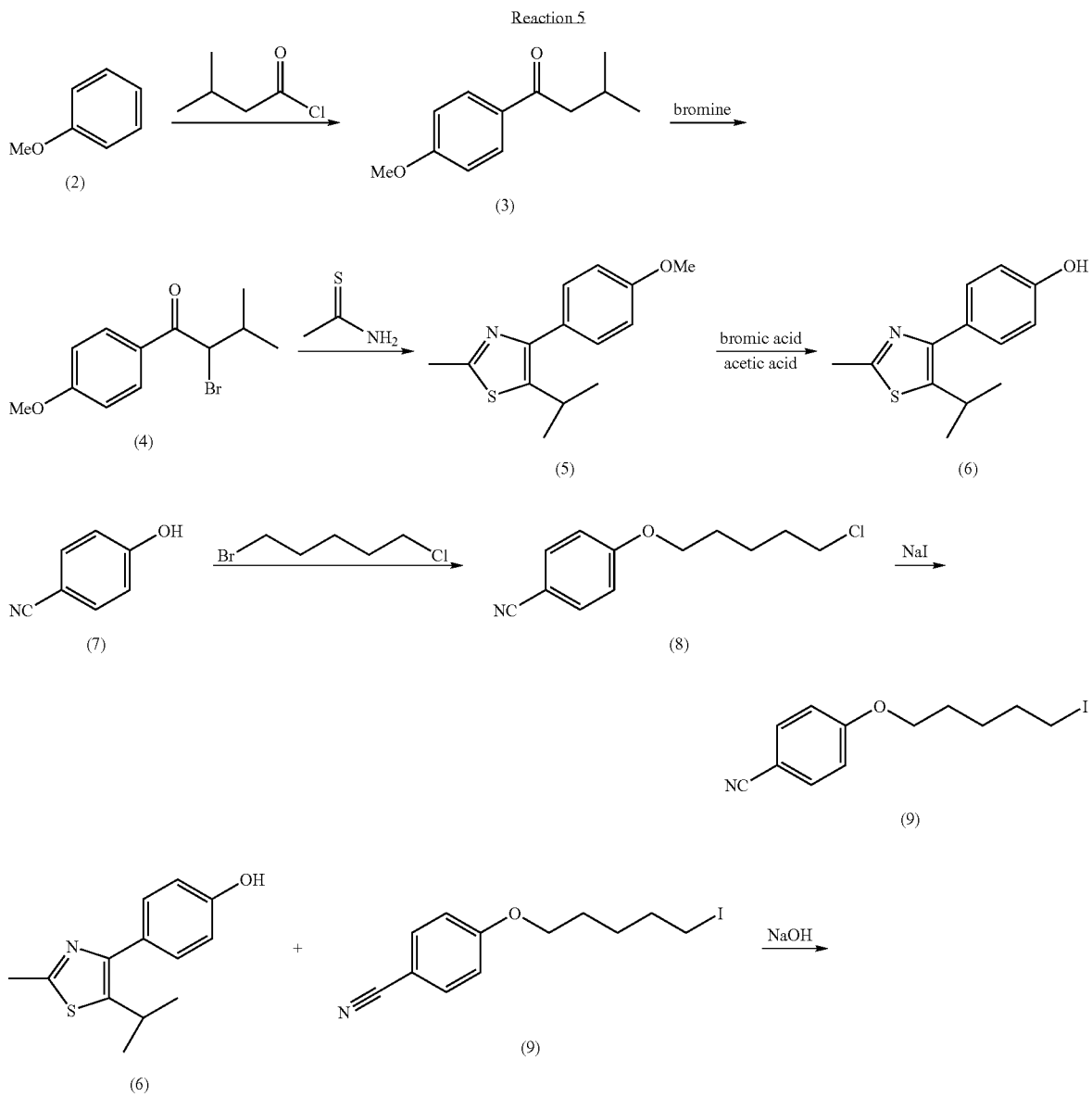

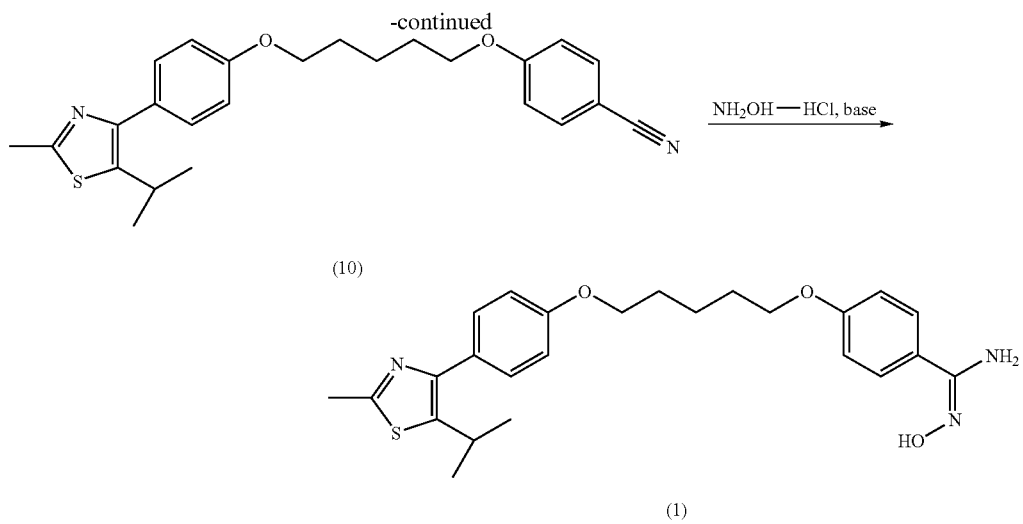

Below, each step of the improved method of preparing N-hydroxy-4-{5-[4-(5-isopropyl-2-methyl-1,3-thiazol-4-yl)phenoxy]pentoxy}benzamidine of the present invention is individually described.

The first to fourth steps are mentioned as above.

In the fifth step, 4-hydroxy-benzonitrile (7) is reacted with 1-bromo-5-chloropentane, giving 4-(5-chloro-pentoxy)-benzonitrile (8) (yield: 90%). At this time, the reaction temperature is preferably maintained in the range from 20 to 82° C., and the reaction solvent is selected from polar solvents, including dichloromethane, acetonitrile, ethylacetate, lower alcohols such as methanol, ethanol or isopropanol, ethers such as tetrahydrofuran or 1,4-dioxane, dimethylformamide, or dimethylsulfoxide, and mixtures thereof. To ensure that the above reaction occurs under a basic condition, an inorganic base, including potassium carbonate, sodium hydroxide, potassium hydroxide, sodium amide, sodium hydride, sodium methoxide, or sodium ethoxide, and other base, may be used. Subsequently, 4-(5-chloro-pentoxy)-benzonitrile (8) is reacted with iodide, thus preparing 4-(5-iodo-pentoxy)-benzonitrile (9) (yield: 99%). As iodide, sodium iodide may be used.

In the sixth and seventh steps, the compound (6) prepared in the fourth step, and the compound (9) prepared in the fifth step are reacted in the presence of sodium hydroxide, thus preparing 4-{5-[4-(5-isopropyl-2-methyl-1,3-thiazol-4-yl)-phenoxy]-pentoxy}-benzonitrile (10) (yield: 94%). The compound (10) is reacted with hydroxylamine hydrochloride and a base, finally obtaining N-hydroxy-4-{5-[4-(5-isopropyl-2-methyl-1,3-thiazol-4-yl)phenoxy]pentoxy}benzamidine (1) (yield: 91%). As such, the reaction solution is directly added with water, thereby being recrystallized, and thus, it may be easily prepared on a large scale.

In the above reaction steps, the reaction temperature is preferably maintained in the range from room temperature to a solvent reflux temperature. The reaction solvent is selected from polar solvents, including dichloromethane, acetonitrile, ethylacetate, lower alcohols such as methanol, ethanol or isopropanol, ethers such as tetrahydrofuran or 1,4-dioxane, dimethylformamide, or dimethylsulfoxide, and mixtures thereof. The base used in the reaction is selected from organic base, including triethylamine, 1,8-diazabicyclo[5.4.0]undec-7-ene, DBU, diethylmethylamine (Et$_2$NMe), N-methylmorpholine, N-methylpiperidine, pyridine, 2,6-dimethylpyridine or from inorganic base, including potassium carbonate, potassium bicarbonate, sodium hydroxide, potassium hydroxide, sodium amide, sodium hydride, sodium methoxide, or sodium ethoxide, and other base. In the present invention, triethylamine is preferable, and is used in 1 to 4 equivalents.

Consequently, the total reaction yield (34%) of the preparation method shown in Reaction 5 was found to be remarkably higher than the total yield (24%) of the method disclosed in the above literature.

As mentioned above, the preparation method of the present invention is economical and simple, and has a high preparation yield, and therefore, is suitable for mass production of N-hydroxy-4-{5-[4-(5-isopropyl-2-methyl-1,3-thiazol-4-yl)phenoxy]pentoxy}benzamidine (1).

A better understanding of the present invention may be obtained through the following examples which are set forth to illustrate, but are not to be construed as the limit of the present invention.

EXAMPLE 1

Preparation of 1-(4-Methoxy-Phenyl)-3-Methyl-Butan-1-One (Compound 3)

While 40 g of isovaleryl chloride and 44 g of aluminum chloride were added to 140 ml of dichloromethane and stirred, 32.6 ml of anisole were slowly added in droplets at −10° C. or lower, and stirring was continued at room temperature for 40 min. Subsequently, 36.6 ml of isovaleryl chloride were slowly added in droplets, and stirring was further continued at room temperature for 18 hr. After the reaction was completed, the resultant reaction mixture was added with 200 ml of dichloromethane, and then washed with a saturated aqueous solution of sodium bicarbonate and water, in that order, after which the dichloromethane layer was dried over anhydrous magnesium sulfate and then concentrated under reduced pressure, thus obtaining 56.9 g (yield: 98.6%) of a title compound as light yellow liquid.

m/z 193[M$^+$+1];

$^1$H NMR(CDCl$_3$) δ(ppm) 0.96(d, 6H), 2.26(m, 1H), 2.75 (d, 2H), 3.84(s, 3H),6.90(d, 2H), 7.92(d, 2H)

EXAMPLE 2

Preparation of 2-bromo-1-(4-Methoxy-Phenyl)-3-Methyl-Butan-1-One (Compound 4)

While 56.9 g of 1-(4-methoxy-phenyl)-3-methyl-butan-1-one (3) prepared in Example 1 were added to 200 ml of ethylacetate and stirred, 18.2 ml of bromine were added at room temperature and stirring was continued at the same temperature for 1 hr. After the reaction was completed, the resultant reaction mixture was washed with brine and water, in that order, after which the ethylacetate layer was dried over anhydrous magnesium sulfate and then concentrated under reduced pressure, thus obtaining 77.0 g (yield: 96.0%) of a title compound as light yellow liquid.

m/z 271[M$^+$];

$^1$H NMR(CDCl$_3$) δ(ppm) 0.97(d, 3H), 1.17(d, 3H), 2.42 (m, 1H), 3.82(s, 3H), 4.86(d, 1H), 6.88(d, 2H), 7.89(d, 2H)

EXAMPLE 3

Preparation of 5-Isopropyl-4-(4-Methoxy-Phenyl)-2-Methyl-1,3-Thiazole (Compound 5)

While 77.0 g of 2-bromo-1-(4-methoxy-phenyl)-3-methyl-butan-1-one (4) prepared in Example 2 were added to 200 ml of ethanol and stirred, 42.7 g of thioacetamide were added. Subsequently, the temperature was gradually increased and stirring under reflux was continued for 22 hr. After the reaction was completed, the resultant reaction mixture was added with 300 ml of ethylacetate, and then washed with a saturated aqueous solution of potassium carbonate. The ethylacetate layer was dried over anhydrous magnesium sulfate, and then concentrated under reduced pressure, thus obtaining 35.8 g (yield: 51.0%) of a title compound as brown liquid.

m/z 248[M$^+$+1];

$^1$H NMR(CDCl$_3$) δ(ppm) 1.28(d, 6H), 2.67(s, 3H), 3.37 (m, 1H), 3.84(s, 3H), 6.94(d, 2H), 7.46(d, 2H)

EXAMPLE 4

Preparation of 4-(5-Isopropyl-2-Methyl-1,3-Thiazol-4-Yl)-Phenol (Compound 6)

While 35.8 g of 5-isopropyl-4-(4-methoxy-phenyl)-2-methyl-1,3-thiazol (5) prepared in Example 3 were added to 86 ml of acetic acid and stirred, 500 ml of 48% bromic acid were added. Subsequently, the temperature was gradually increased and stirring under reflux was continued for 18 hr. The temperature was decreased to room temperature, and 400 ml of dichloromethane were added and stirring was further continued for 30 min. Then, the dichloromethane layer was removed. Thereafter, the obtained reaction solution was added with a saturated aqueous solution of potassium carbonate to be neutralized at pH 7-8, after which the precipitated solid was filtered and then washed with water, thus obtaining 28.4 g (yield: 84%) of a title compound as a solid.

m.p. 165° C.;

m/z 234[M$^+$+1];

$^1$H NMR(CDCl$_3$) δ(ppm) 1.29(d, 6H), 2.72(s, 3H), 3.38 (m, 1H), 7.42(d, 2H), 7.28(d, 2H)

EXAMPLE 5

Preparation of 4-(5-Chloro-Pentoxy)-Benzonitrile (Compound 8)

While 70 g of 4-hydroxybenzonitrile (7) were added to 500 ml of acetonitrile and stirred, 85.3 g of potassium carbonate and 77.4 ml of 1-bromo-5-chloropentane were added. Subsequently, the temperature was gradually increased and stirring under reflux was continued for 8 hr, and then stirring was further continued at room temperature for 18 hr. After the reaction was completed, the resultant reaction mixture was added with 500 ml of ethylacetate and then washed with water. Thereafter, the ethylacetate layer was dried over anhydrous magnesium sulfate, and then concentrated under reduced pressure. The concentrated compound was dissolved in 280 ml of methanol, stirred at 0° C. for 2 hr, and then filtered, thus obtaining 118 g (yield: 90%) of a title compound as a white solid.

m.p. 47° C.;

m/z 224[M$^+$+1];

$^1$H NMR(CDCl$_3$) δ(ppm) 1.64(m, 2H), 1.82(m, 4H), 3.57 (t, 2H), 4.01(t, 2H), 6.93(d, 2H), 7.57(d, 2H)

EXAMPLE 6

Preparation of 4-(5-Iodo-Pentoxy)-Benzonitrile (Compound 9)

While 50 g of 4-(5-chloro-pentoxy)-benzonitrile (8) prepared in Example 5 were added to 500 ml of 2-butanone and stirred, 167 g of sodium iodide were added. Subsequently, the reaction temperature was gradually increased and stirring was continued at 70-80° C. for 6 hr. After the reaction was completed, the reaction temperature was decreased to room temperature, and the resultant reaction mixture was added with 1 L of ethylacetate, and then washed with water and brine. The ethylacetate layer was dried over anhydrous magnesium sulfate, and then concentrated under reduced pressure. The residual solution was crystallized with methylalcohol, thus obtaining 69.7 g (yield: 99%) of a title compound as a white solid.

m.p. 61° C.

m/z 316[M$^+$+1];

$^1$H NMR(CDCl$_3$) δ(ppm) 1.54(m, 2H), 1.87(m, 4H), 3.22 (t, 2H), 3.98(t, 2H), 6.93(d, 2H), 7.57(d, 2H)

EXAMPLE 7

Preparation of 4-{5-[4-(5-Isopropyl-2-Methyl-1,3-Thiazol-4-Yl)-Phenoxy]-Pentoxy}-Benzonitrile (Compound 10)

While 72.6 g of 4-(5-isopropyl-2-methyl-1,3-thiazol-4-yl)-phenol (6) prepared in Example 4 were added to 850 ml of dimethylformamide and stirred, 15.0 g of sodium hydroxide were added. The reaction temperature was gradually increased and stirring was continued at 50-55° C. for 30 min. Thereafter, 70.0 g of 4-(5-chloro-pentoxy)-benzonitrile (8), prepared in Example 5, or 95.3 g of 4-(5-iodo-pentoxy)-benzonitrile (9), prepared in Example 6, were added. The reaction temperature was gradually increased and stirring was continued at 80-90° C. for 3 hr. After the reaction was completed, the temperature was decreased to room temperature, and the resultant reaction mixture was added with 850 ml of ethylacetate, and then washed with water and brine. Subsequently, the ethylacetate layer was dried over anhydrous magnesium sulfate, and then concentrated under reduced pressure. The residual solution was crystallized with ethylacetate and n-hexane, thus obtaining 114 g (yield: 90%) of a title compound as a light yellow solid through the reaction with the compound (8), or 119.6 g (yield: 94%) of a title compound as a light yellow solid through the reaction with the compound (9).

m.p. 173° C.;

m/z 421[M$^+$+1];

$^1$H NMR(CDCl$_3$) δ(ppm) 1.28(d, 6H), 1.66(m, 2H), 1.87 (m, 4H), 2.67(s, 3H), 3.35(m, 1H), 4.01(m, 4H), 6.93(d, 4H), 7.46(d, 2H), 7.56(d, 2H)

EXAMPLE 8

Preparation of N-Hydroxy-4-{5-[4-(5-Isopropyl-2-Methyl-1,3-Thiazol-4-Yl)Phenoxy]Pentoxy}Benzamidine (Compound 1)

While 45 g of 4-5-[4-(5-isopropyl-2-methyl-1,3-thiazol-4-yl)-phenoxy]-pentoxy-benzonitrile (10) prepared in Example 6 were added to 300 ml of ethanol and stirred, 15 g of hydroxylamine hydrochloride and 30 ml of triethylamine were added. The temperature was gradually increased and stirring under reflux was continued for 15 hr. After the reaction was completed, the temperature was decreased to 40° C., and the resultant reaction solution was slowly added with water, thereby being crystallized. The precipitated solid was filtered and washed with water, thus obtaining 44.2 g (yield: 95%) of a title compound as a white solid.

m.p. 97° C.;

m/z 454[M$^+$+1];

$^1$H NMR(DMSO-d$_6$) δ(ppm) 1.22(d, 6H), 1.57(m, 2H), 1.78(m, 4H), 2.59(s, 3H), 3.33(m, 1H), 4.00(m, 4H), 5.72(s, 2H), 6.90(d, 2H), 6.98(d, 2H), 7.42(d, 2H), 7.57(d, 2H)

INDUSTRIAL APPLICABILITY

As described above, the present invention provides an improved method of preparing N-hydroxy-4-{5-[4-(5-isopropyl-2-methyl-1,3-thiazol-4-yl)phenoxy]pentoxy}benzamidine. The preparation method of the present invention is advantageous because it has simpler reaction processes than conventional methods, and also, it adopts a recystallization process, which is easier than conventional purification techniques and is suitable for mass production, thereby greatly increasing the purity and preparation yield.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing N-hydroxy-4-{5-[4-(5-isopropyl-2-methyl-1,3-thiazol-4-yl)phenoxy]pentoxy}benzamidine (1), comprising steps of:

1) reacting anisole (2) with isovaleryl chloride, to prepare 1-(4-methoxy-phenyl)-3-methyl-butan-1-one (3);
2) reacting the compound (3) prepared in step 1) with bromine, sulfuryl chloride, N-bromosuccinimide or copper bromide, to prepare 2-bromo-1-(4-methoxy-phenyl)-3-methyl-butan-1-one (4);
3) reacting the compound (4) prepared in step 2) with thioacetamide, to prepare 5-isopropyl-4-(4-methoxy-phenyl)-2-methyl-thiazole (5);
4) reacting the compound (5) prepared in step 3) with bromic acid and acetic acid, sodium cyanide and dimethylsulfoxide, or tetrabutylammonium iodide and boron trifluoride•diethylether, to prepare 4-(5-isopropyl-2-methyl-1,3-thiazol-4-yl)-phenol (6);
5) reacting the compound (6) obtained in step 4) with 4-(5-chloro-pentoxy)-benzonitrile (8) or with 4-(5-iodo-pentoxy)-benzonitrile (9), to prepare 4-{5-[4-(5-isopropyl-2-methyl-1,3-thiazol-4-yl)-phenoxy]-pentoxy}-benzonitrile (10), and
6) reacting the compound (10) prepared in step 5) with hydroxylamine hydrochloride and a base, to prepare N-hydroxy-4-{5-[4-(5-isopropyl-2-methyl-1,3-thiazol-4-yl)phenoxy]pentoxy}benzamidine (1).

2. The method according to claim 1, wherein, in step 5), 4-hydroxy-benzonitrile (7) is reacted with 1-bromo-5-chloropentane to afford 4-(5-chloro-pentoxy)-benzonitrile (8), which is then reacted with the compound (6) obtained in step 4) in the presence of sodium hydroxide, to prepare 4-{5-[4-(5-isopropyl-2-methyl-1,3-thiazol-4-yl)-phenoxy]-pentoxy}-benzonitrile (10).

3. The method according to claim 1, wherein, in step 5), 4-hydroxy-benzonitrile (7) is reacted with 1-bromo-5-chloropentane to afford 4-(5-chloro-pentoxy)-benzonitrile (8), which is then reacted with iodide to afford 4-(5-iodo-pentoxy)-benzonitrile (9), which is then reacted with the compound (6) obtained in step 4) in the presence of sodium hydroxide, to prepare 4-{5-[4-(5-isopropyl-2-methyl-1,3-thiazol-4-yl)-phenoxy]-pentoxy}-benzonitrile (10).

4. The method according to claim 1, wherein, in step 2), the compound (3) prepared in step 1) is reacted with bromine, to prepare 2-bromo-1-(4-methoxy-phenyl)-3-methyl-butan-1-one (4).

5. The method according to claim 1, wherein, in step 4), the compound (5) prepared in step 3) is reacted with bromic acid and acetic acid, to prepare 4-(5-isopropyl-2-methyl-1,3-thiazol-4-yl)-phenol (6).

6. The method according to claim 1, wherein the base used in step 6) is selected from the group consisting of triethylamine, 1,8-diazabicyclo[5.4.0]undec-7-ene, DBU, diethylmethylamine (Et$_2$NMe), N-methylmorpholine, N-methylpiperidine, pyridine, 2,6-dimethylpyridine, potassium carbonate, potassium bicarbonate, sodium hydroxide, potassium hydroxide, sodium amide, sodium hydride, sodium methoxide, and sodium ethoxide.

7. The method according to claim 6, wherein the base is triethylamine.

* * * * *